United States Patent
Ball (10) Patent No.: US 7,534,270 B2
(45) Date of Patent: May 19, 2009

(54) MODULAR TOTAL ANKLE PROSTHESIS APPARATUSES AND METHODS

(75) Inventor: Robert J. Ball, San Marcos, CA (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 594 days.

(21) Appl. No.: 10/932,493

(22) Filed: Sep. 2, 2004

(65) Prior Publication Data

US 2005/0049711 A1 Mar. 3, 2005

Related U.S. Application Data

(60) Provisional application No. 60/499,760, filed on Sep. 3, 2003.

(51) Int. Cl.
*A61F 2/42* (2006.01)
(52) U.S. Cl. .................................. 623/21.18
(58) Field of Classification Search ... 623/21.11–21.19, 623/18.11
See application file for complete search history.

(56) References Cited

U.S. PATENT DOCUMENTS

| | | |
|---|---|---|
| 3,839,742 A | 10/1974 | Link |
| 3,872,519 A | 3/1975 | Giannestras et al. |
| 3,886,599 A | 6/1975 | Schlein |
| 3,889,300 A | 6/1975 | Smith |
| 3,896,502 A | 7/1975 | Lennox |
| 3,896,503 A | 7/1975 | Freeman et al. |
| 3,975,778 A | 8/1976 | Newton, III |
| 3,987,500 A | 10/1976 | Schlein |
| 4,016,606 A | 4/1977 | Murray et al. |
| 4,021,864 A | 5/1977 | Waugh |
| 4,069,518 A | 1/1978 | Groth, Jr. et al. |
| 4,069,528 A * | 1/1978 | Newton et al. .................. 7/170 |
| 4,085,466 A | 4/1978 | Goodfellow et al. |

(Continued)

OTHER PUBLICATIONS

International Search Report for corresponding International Application No. PCT/US05/29726 dated Dec. 18, 2006.

(Continued)

*Primary Examiner*—Alvin J. Stewart
(74) *Attorney, Agent, or Firm*—Jenkins, Wilson, Taylor & Hunt, P.A.

(57) ABSTRACT

Ankle implant systems and methods are provided that can allow a surgeon to select the type of prosthesis desired during an ankle surgical operation. The surgeon can implant a set of standardized fixation components into the tibia and/or fibula bones and the talus bone. Once implanted, the surgeon can select a bearing component from a number of bearing components that allow for different size patients, but also modify the manner in which the prosthesis functions (either semiconstrained or unconstrained). In one embodiment, an ankle implant can include a talar component having a lower surface with a bone fixation portion for fixation to a talus bone. A tibial component has an upper surface with a bone fixation portion for fixation of the tibial component to a tibia bone and/or a fibula bone, and the tibial component also has a lower surface with at least one protrusion extending from the lower surface. A bearing component is included between the tibial and talar components and has a lower surface for cooperative engagement with an upper surface of the talar component. The protrusion of the tibial component is adapted to engage a recess of the bearing component to desirably limit rotational and translational movement of the tibial component relative to the bearing component.

9 Claims, 7 Drawing Sheets

U.S. PATENT DOCUMENTS

| | | | | |
|---|---|---|---|---|
| 4,156,944 | A | 6/1979 | Schreiber et al. | |
| 4,207,627 | A | 6/1980 | Cloutier | |
| 4,209,861 | A | 7/1980 | Walker et al. | |
| 4,224,697 | A | 9/1980 | Murray et al. | |
| 4,232,404 | A * | 11/1980 | Samuelson et al. | 623/21.18 |
| 4,309,778 | A | 1/1982 | Buechel et al. | |
| 4,340,978 | A | 7/1982 | Buechel et al. | |
| 4,470,158 | A * | 9/1984 | Pappas et al. | 623/20.21 |
| 4,755,185 | A | 7/1988 | Tarr | |
| 4,759,766 | A | 7/1988 | Buettner-Janz et al. | |
| 4,792,340 | A | 12/1988 | Aulie et al. | |
| 5,314,485 | A * | 5/1994 | Judet | 623/21.13 |
| 5,326,365 | A * | 7/1994 | Alvine | 623/21.18 |
| 5,387,240 | A * | 2/1995 | Pottenger et al. | 623/20.29 |
| 5,514,139 | A | 5/1996 | Goldstein et al. | |
| 5,597,379 | A | 1/1997 | Haines et al. | |
| 5,609,639 | A * | 3/1997 | Walker | 623/20.29 |
| 5,609,644 | A * | 3/1997 | Ashby et al. | 623/20.2 |
| 5,643,272 | A | 7/1997 | Haines et al. | |
| 5,755,801 | A * | 5/1998 | Walker et al. | 623/20.21 |
| 5,755,803 | A | 5/1998 | Haines et al. | |
| 5,766,259 | A * | 6/1998 | Sammarco | 623/21.18 |
| 5,810,827 | A | 9/1998 | Haines et al. | |
| 5,824,106 | A * | 10/1998 | Fournol | 623/21.18 |
| 5,879,354 | A | 3/1999 | Haines et al. | |
| 6,039,764 | A | 3/2000 | Pottenger et al. | |
| 6,056,754 | A | 5/2000 | Haines et al. | |
| 6,080,195 | A | 6/2000 | Colleran et al. | |
| 6,090,144 | A * | 7/2000 | Letot et al. | 623/20.34 |
| 6,099,570 | A * | 8/2000 | Livet et al. | 623/20.21 |
| 6,117,175 | A | 9/2000 | Bosredon | |
| 6,123,728 | A | 9/2000 | Brosnahan et al. | |
| 6,162,254 | A | 12/2000 | Timoteo | |
| 6,165,223 | A | 12/2000 | Metzger et al. | |
| 6,183,519 | B1 * | 2/2001 | Bonnin et al. | 623/21.18 |
| 6,197,064 | B1 | 3/2001 | Haines et al. | |
| 6,203,576 | B1 * | 3/2001 | Afriat et al. | 623/20.27 |
| 6,210,444 | B1 | 4/2001 | Webster et al. | |
| 6,210,445 | B1 * | 4/2001 | Zawadzki | 623/20.33 |
| 6,217,618 | B1 | 4/2001 | Hileman | |
| 6,299,646 | B1 | 10/2001 | Chambat et al. | |
| 6,409,767 | B1 * | 6/2002 | Perice et al. | 623/21.18 |
| 6,413,279 | B1 | 7/2002 | Metzger et al. | |
| 6,443,991 | B1 | 9/2002 | Running | |
| 6,475,241 | B2 | 11/2002 | Pappas | |
| 6,485,520 | B1 * | 11/2002 | Hubach et al. | 623/21.13 |
| 6,695,848 | B2 | 2/2004 | Haines | |
| 6,875,222 | B2 | 4/2005 | Long et al. | |
| 6,939,380 | B2 * | 9/2005 | Guzman | 623/21.18 |
| 7,011,687 | B2 | 3/2006 | Deffenbaugh et al. | |
| 7,025,790 | B2 * | 4/2006 | Parks et al. | 623/21.18 |
| 7,323,012 | B1 * | 1/2008 | Stone et al. | 623/21.18 |
| 7,465,319 | B2 * | 12/2008 | Tornier | 623/19.11 |
| 2001/0014827 | A1 * | 8/2001 | Chambat et al. | 623/20.33 |
| 2003/0181985 | A1 * | 9/2003 | Keller et al. | 623/21.18 |
| 2003/0187511 | A1 | 10/2003 | Ball et al. | 623/21.13 |
| 2003/0204265 | A1 * | 10/2003 | Short et al. | 623/21.18 |
| 2003/0216813 | A1 | 11/2003 | Ball et al. | 623/21.12 |
| 2004/0002768 | A1 * | 1/2004 | Parks et al. | 623/21.18 |
| 2004/0138756 | A1 * | 7/2004 | Reeder | 623/21.11 |
| 2004/0186585 | A1 * | 9/2004 | Feiwell | 623/21.18 |
| 2005/0049711 | A1 | 3/2005 | Ball | |
| 2005/0171613 | A1 * | 8/2005 | Sartorius et al. | 623/21.13 |
| 2005/0182492 | A1 * | 8/2005 | Pappas et al. | 623/21.18 |
| 2006/0015109 | A1 | 1/2006 | Haines | |
| 2006/0015115 | A1 | 1/2006 | Haines | |
| 2006/0015116 | A1 | 1/2006 | Haines | |
| 2006/0015117 | A1 | 1/2006 | Haines | |
| 2006/0030853 | A1 | 2/2006 | Haines | |
| 2006/0030854 | A1 | 2/2006 | Haines | |
| 2006/0030855 | A1 | 2/2006 | Haines | |
| 2006/0030944 | A1 | 2/2006 | Haines | |
| 2006/0030946 | A1 * | 2/2006 | Ball et al. | 623/21.13 |
| 2006/0058882 | A1 | 3/2006 | Haines | |
| 2006/0136062 | A1 | 6/2006 | DiNello et al. | |
| 2006/0161260 | A1 * | 7/2006 | Thomas et al. | 623/21.12 |
| 2007/0112431 | A1 * | 5/2007 | Kofoed | 623/21.18 |
| 2007/0162137 | A1 * | 7/2007 | Kloss et al. | 623/17.15 |

OTHER PUBLICATIONS

International Preliminary Report on Patentability for corresponding International Application No. PCT/US05/29726 dated Mar. 1, 2007.

Office Action-Restriction Requirement dated Sep. 19, 2006 for U.S. Appl. No. 11/207,597.

Office Action-non final action dated Aug. 14, 2007 for U.S. Appl. No. 11/207,597.

Office Action non final action dated Jan. 10, 2007 for U.S. Appl. No. 11/207,597.

Office Action final action dated Mar. 17, 2008 for U.S. Appl. No. 11/207,597.

Office Action non final action dated Jul. 11, 2008 for U.S. Appl. No. 11/207,597.

* cited by examiner

MODULAR TOTAL ANKLE PROSTHESIS APPARATUSES AND METHODS

RELATED APPLICATIONS

This application claims the benefit of U.S. Provisional Patent Application Ser. No. 60/499,760, filed Sep. 3, 2003; the disclosure of which is incorporated herein by reference in its entirety.

TECHNICAL FIELD

The present subject matter is directed generally to total ankle prosthesis apparatuses and methods. More specifically, the present subject matter is directed to a system and method for ankle prosthesis apparatuses and methods having a plurality of components, the selection of which determines the extent of freedom of movement allowed.

BACKGROUND ART

The concept of total ankle arthroplasty has a long and relatively unsuccessful history. Only recently has total ankle arthroplasty regained some recognition as a viable treatment for limited indications. Replacement of the ankle joint is particularly problematic due to the relatively small articular surfaces, complex biomechanics, and limited access to the joint during replacement, and wide variation in patient candidacy. These factors have led to post-operative complications such as loosening, subsidence, pain, and prosthetic wear. In addition to these technical difficulties, regulatory agencies have classified ankle prosthetics in a manner substantially limiting scientific progress in ankle replacement due to the financial burden of obtaining market clearance for such devices. What is needed is an ankle prosthetic system or kit that can sufficiently address all types of surgical candidates considered for total ankle replacement. The kit must provide means to adjust the fixation and articular adjustment such that modifications to the "fit" and "function" of the prosthesis can be made intraoperatively or interoperatively (i.e. within the same or in a separate operation). Further the kit must provide means for legal distribution of the device depending on the legal and/or regulatory constraints place on such devices and the geographic location of use.

Other ankle prosthetics currently marketed include the following:

| Company | Device Name | Patent(s) | Type |
| --- | --- | --- | --- |
| DePuy | Alvine/Agility | 5,326,365 | Semi |
| EndoTech | BP (Buechel, Pappas) | 4,309,778 | Unconstrained |
| LINK | S.T.A.R. | unknown | Unconstrained |
| Tornier | Unknown | 5,824,106: 6,183,519 | Unconstrained |

The key element in the chart above is the type of prosthesis. Two types of prosthetics are generally available: Semi-constrained, and unconstrained. Both types of prosthetics make use of a 3-component design: upper, middle, and lower component (tibial, bearing, and talar component, respectively).

A semiconstrained prosthesis such as the Alvine device provides for a tibial fixation component (metal), which provides firm attachment to the distal end of the tibial bone. A talar component provides firm attachment to the proximal end of the talar bone, and provides on its upper or proximal side a generally convex surface for articulation. Into the tibial component fits a UHMWPE bearing that intimately fits into a socket formed to receive the bearing. The two components fit together such that no motion is considered between the bearing and the tibial component. The underside of the bearing provides a generally concave surface to articulate with the convex surface of the talar component. The radii of curvature of these curved surfaces are mismatched such that all motions present in a nature ankle can be at least partially replicated. These motions include plantar/dorsiflexion, rotation about the tibial axis, medial/lateral translation, and anterior/posterior translation. Rotations in the frontal region are not well supported as there is little curvature in this region. These motions (they can occur actively) lead to edge loading, causing higher stress and greater propensity for wear. Also, as the articular surfaces are designed for mismatch, even under optimum implant positioning and loading, higher stress will be seen at the contact point due to the point loading associated with mismatched radii.

The unconstrained prosthetics are all generally the same in function. They are similar to the semiconstrained prostheses except that there is designed into the prosthesis the potential for motion between the tibial tray component and the bearing. There is no intimate fit between the bearing and the tibial component; the tibial component has a flat undersurface and the bearing has a simple flat upper surface so that translation and rotation are allowed at this interface. Further, the curvature of the interface between the talar component and the bearing are matched, so there is a large contact surface area and optimized contact stress (reduced wear). This match articulation can be accomplished because other motions are allowed for between the tibial and bearing components. It has been clearly shown with clinical history in all joints that if these motions are not allowed for, the force must be absorbed at the implant bone interface, and can lead to a greater propensity for loosening.

Another known device is described in U.S. Pat. No. 5,824,106 (hereafter the '106 Patent) to Fournol, which describes an ankle prosthesis having a tibial component with an articular surface that slides on an intermediate element, which in turn has a recess for accommodating a protrusion or lug of a talar component. The '106 Patent, aside from differing substantially from the embodiments of the present subject matter, does not contemplate selecting the intermediate component from a plurality of components, each having a differently shaped recess for meeting a recipient's ambulatory needs and for overcoming the legal obstacles of different regions.

It has been commonly considered to have a kit that allows a surgeon to select from varying sized or thickness of bearings. However, it has not been known thus far to have the option of selecting from a plurality of bearings that allow one to control, in varying amounts, the amount of motion allowable between the potential articular surfaces.

Further, it must be noted that the Food and Drug Administration (FDA) currently classifies unconstrained ankle prostheses as class III devices. Under FDA regulations, class III devices require Pre-Market Approval (PMA) prior to distribution in the US. This further means the clinical data must be provided that can substantial the efficacy of the new medical device. This clinical data is increasingly expensive to develop and in most cases prevents a particular project from being financially viable. The semiconstrained device is a class II device, and typically does not require PMA, but substantial equivalency to a currently approved device. There are currently no legally marketed ankle prostheses in the US.

SUMMARY

An ankle implant system or kit and method are provided that can provide a surgeon the option of selecting the type of prosthesis desired during a surgical operation. The surgeon can implant a set of standardized fixation components into the tibia and/or fibula bones and the talus bone. Once implanted, the surgeon can select a bearing component from a plurality of bearing components that allow for different size patients, but also modify the manner in which the prosthesis functions (either semiconstrained or unconstrained). This decision can be made on a variety of patient factors as well as legal factors depending on the particular case.

It is therefore an object to provide novel apparatuses and methods for an ankle implant or prosthesis system. An object having been stated hereinabove, and which is addressed in whole or in part by the present subject matter, other objects will become evident as the description proceeds when taken in connection with the accompanying drawings as best described hereinbelow.

DETAILED DESCRIPTION

Figure 1:
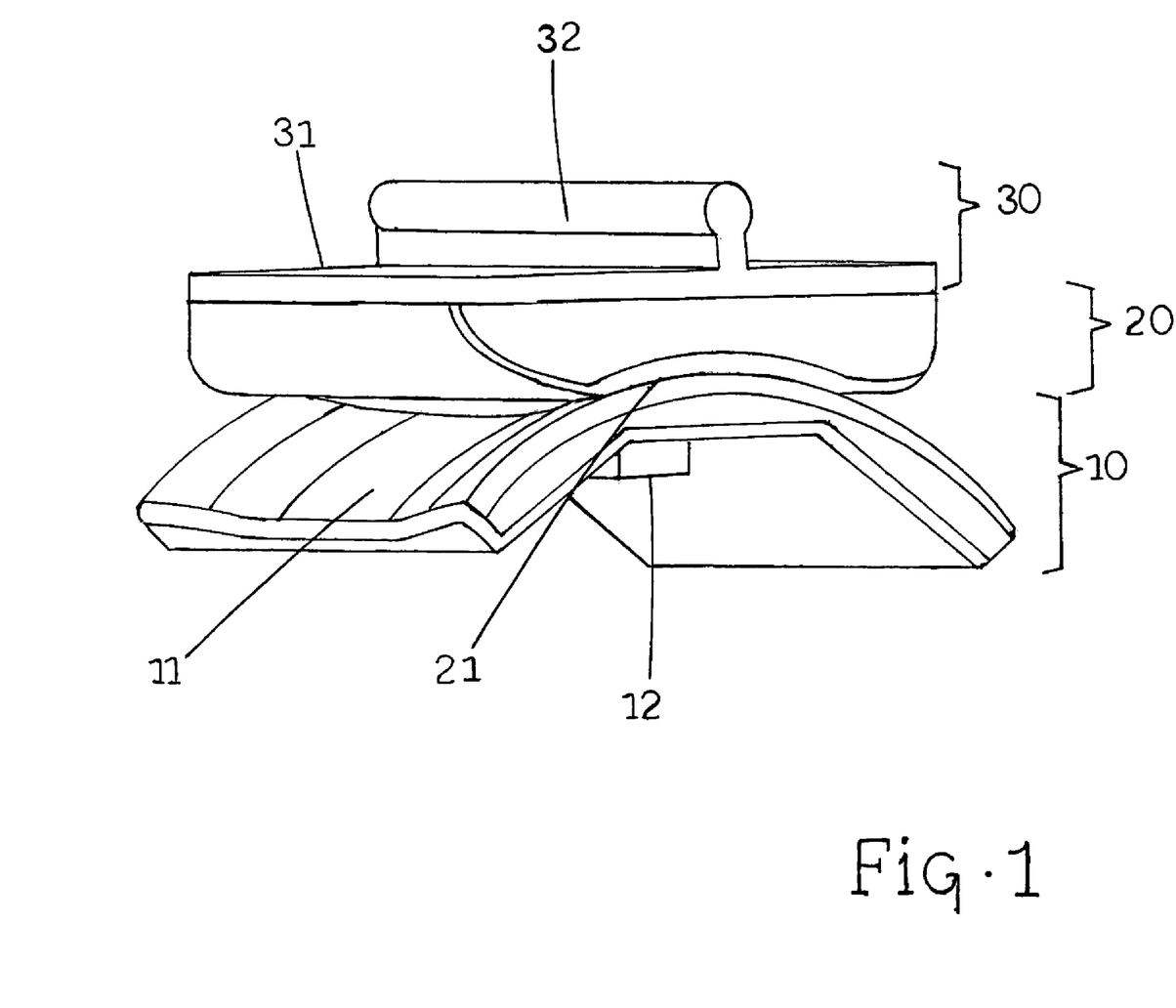
FIG. 1 of the drawings illustrates an isometric view of a typical embodiment of the present subject matter.

FIG. 1 illustrates a total ankle joint replacement prosthesis 1 comprising three components: a talar component 10, a tibial component 30, and a bearing 20 disposed therebetween. It is envisioned that one or more of these components could be formed of separable components as desired and as can be appreciated by those of skill in the art.

Figure 2:
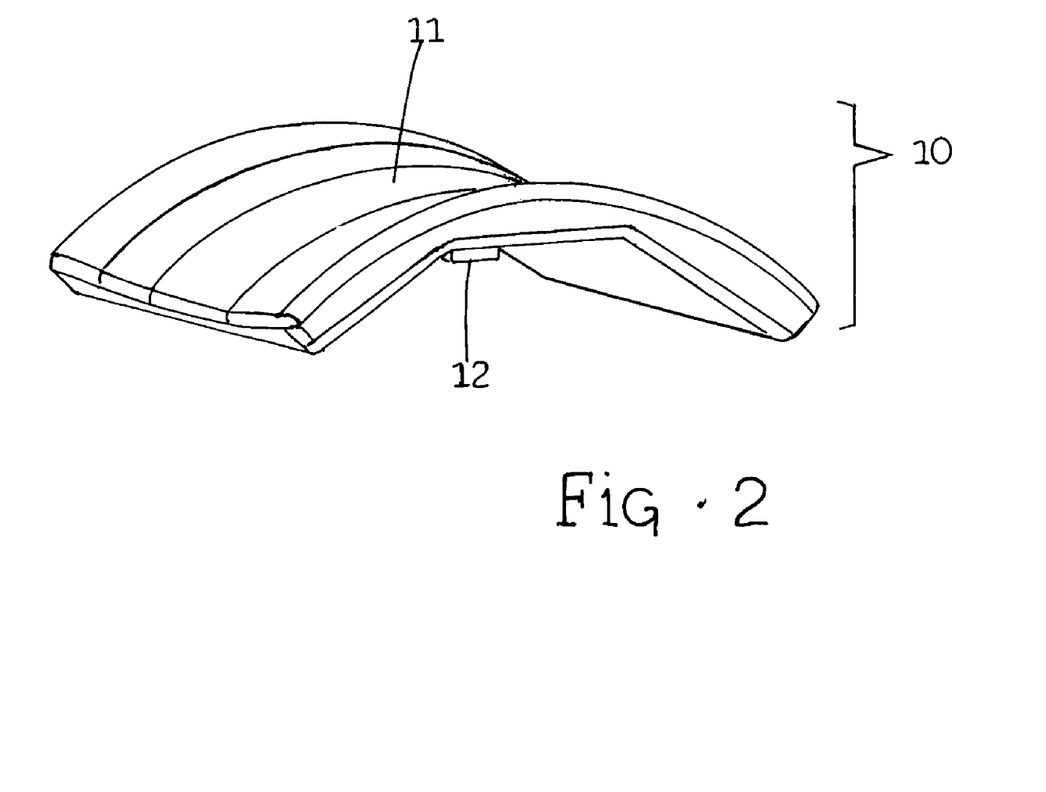
FIG. 2 of the drawings illustrates an isometric view of the tibial component of FIG. 1.
Figure 3:
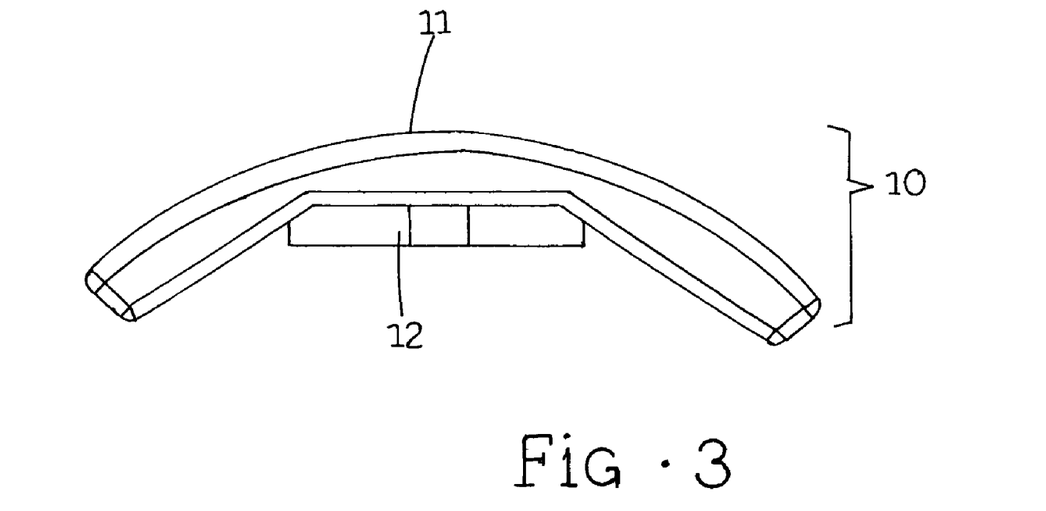
FIG. 3 of the drawings illustrates a bottom view of the tibial component of FIG. 1.

Talar component 10 can preferably be made from any suitable material such as a metallic material such as cobalt-chrome or titanium alloy, or other biologically stable material. As shown in FIGS. 2 and 3, talar component 10 can have an upper surface with a suitably shaped surface, such as saddle shaped surface 11, for articulation with bearing component 20. Saddle shaped surface 11 can have a convex shape when viewed laterally and a concave shape when viewed from the anterior or posterior. The dimensions and arrangement of this surface can vary suitably as can be appreciated by those of skill in the art depending on the motions desired in the final prosthesis. Also, this surface can be shaped otherwise, such as, for example, more elliptically as in a bi-radial surface. There is also a bone fixation portion 12 for placement and sacrament into bone, such as the talus bone. Bone fixation portion 12 shown in the FIGS. 1, 2 and 3 is substantially in the form of a rib but can be any suitable form such as, for example, the form of stems, pegs, blocks, spikes, screws, pins, etc.

Figure 4:
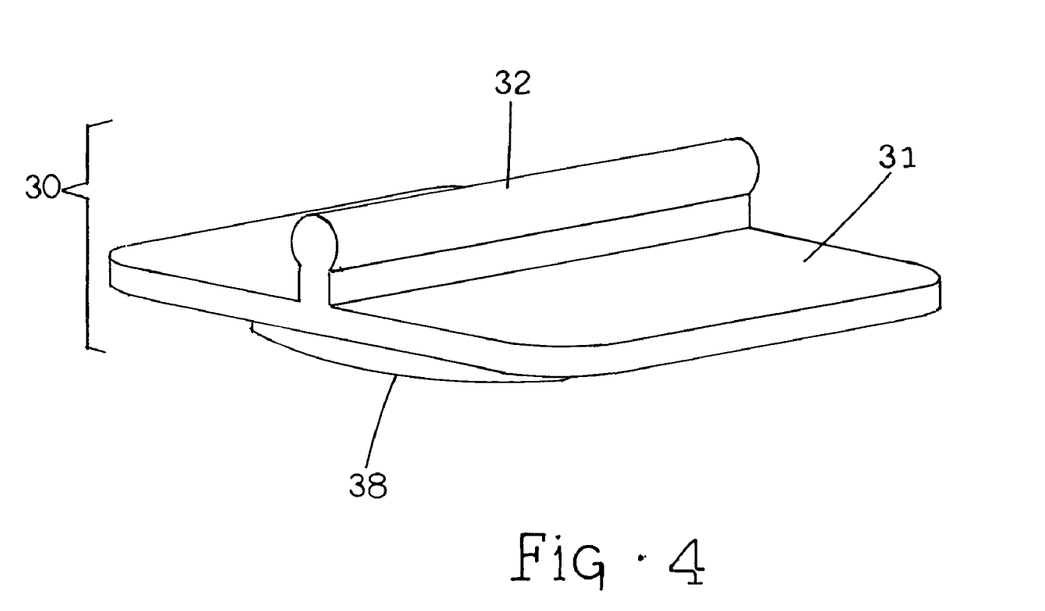
FIG. 4 of the drawings illustrates an isometric view of a bearing component according to one embodiment of the present subject matter.
Figure 5:
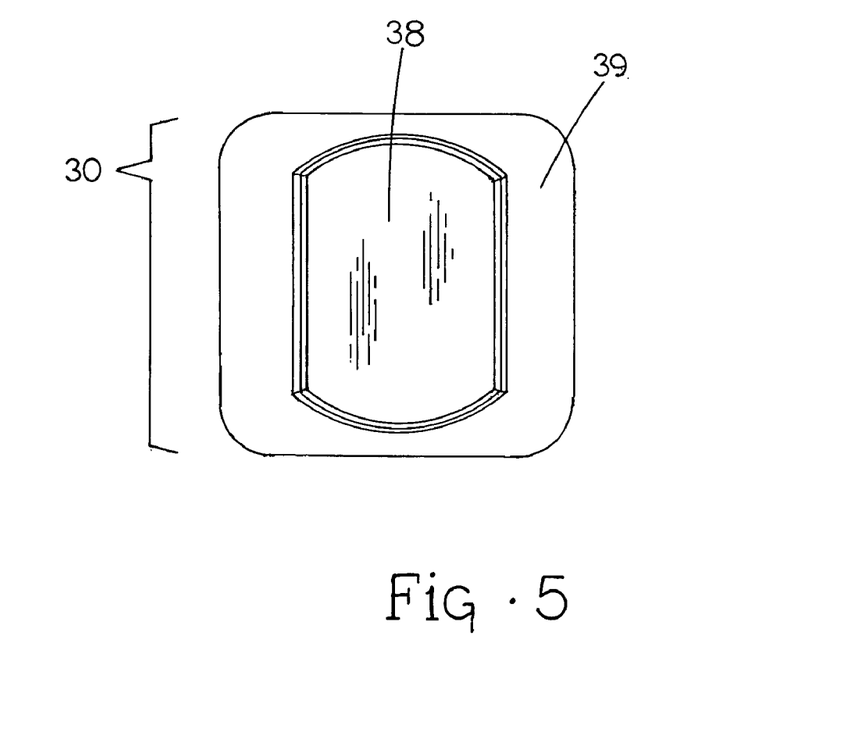
FIG. 5 of the drawings illustrates an isometric view of a bearing component according to another embodiment of the present subject matter.

FIGS. 4 and 5 illustrate an upper or tibial component 30 for fixation into bone such as the tibia bone. Tibial component 30 can also made of any suitable material, such as a metallic material as with talar component 10. On its upper surface 31, there is shown a bone fixation portion 32 that is adapted for fixation into bone such as the tibia bone and/or fibula bone. Bone fixation portion 32 is shown as a bar but can be any suitable form, as with talar component 10, depending on indications for the patient. On upper surface 31, a series of ribs and/or patches can exist for a porous coating or other fixation enhancing treatment or coatings to exist. Such coating or coatings could be placed in the patches, which separate the ribs. In this manner, tibial component 30 can be made as thin as possible to facilitate minimal bone resection, while maintaining the ability to add fixation enhancement features.

On bottom or lower surface 39 of tibial component 30, a structure such as at least one protrusion 38 exists for guidance of articulation between tibial component 30 and bearing component 20. Protrusion 38 is adapted to fit within a pocket or recess 23 (shown best in FIG. 6) defined in bearing component 20, to facilitate a designed type of motion as described below. Lower surface 39 of tibial component 30 and protrusion 38 can be highly polished to facilitate a minimum wear situation. In one embodiment, lower surface 39 can be flat.

Figure 6:
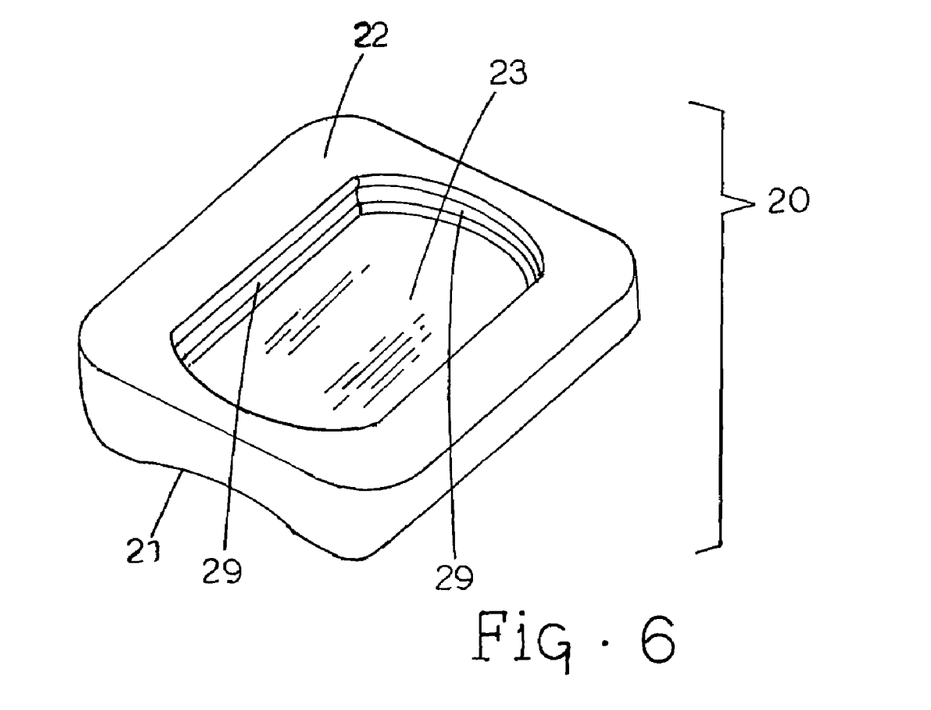
FIG. 6 of the drawings illustrates an isometric view of the tibial component of FIG. 1.

FIG. 6 illustrates one type of bearing component 20 that can be placed between tibial component 30 and talar component 10. Bearing component 20 can be made preferably of a suitable plastic material such as UHMWPE or similar biologically stable material. Lower surface 21 of bearing component 20 can be complementarily shaped to at least substantially match or matingly engage with convex surface 11 of the talar component. The radius of this concave surface 21 can be adjusted to mate with convex surface 11 in a manner that can provide or allow desired range of motion. Concave surface 21 could have a curved surface making a spherical or cup shape. The concavity of this surface can be created by one full radius, multiple tangent radii, or constantly varying radii, so long as to provide efficient means of articulation. Upper surface 22 of bearing component 20 can define recess 23 designed to accommodate such as by fitting with, matching or matingly engaging protrusion 38 of tibial component 30. In the form shown in FIG. 6, the diameter and width of recess 23 substantially matches that of protrusion 38 of tibial component 30. In this form, during operation of the prosthesis, there would be no substantial motion between tibial component 30 and bearing component 20. In this form, the construct of the 3-joint component forms what would be called a semi-constrained prosthesis.

The height of the prosthesis can also be adjusted to modify to resolved motion during the operation. The prosthesis can provide for varying thickness bearings, which allows for tensioning of joint tissues during the operation, thus enhancing the potential for joint prosthesis longevity, etc.

Figure 7:
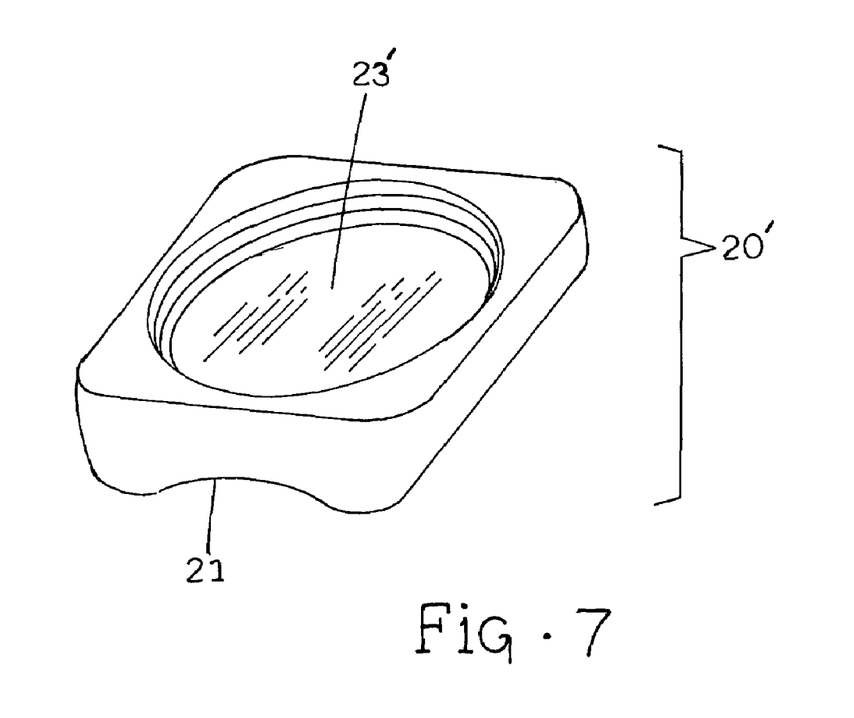
FIG. 7 of the drawings illustrates a side view of the tibial component of FIG. 1.

In another form, bearing component 20' and recess 23' as shown in FIG. 7 can be made of substantially the same depth and diameter as that of the pocket 23 of bearing 20. However, opposing, flat sides 29 of bearing component 20 are absent in bearing component 20'. In this manner, the rotation motion about the axis of diameter would not be restricted. In this form, the radius may be adjusted to mate with the convex shape in a more conforming (more restricted) manner. This allows for a greater surface area of contact, and thus theoretically reduced contacted stresses in the polyethylene bearing component 20'. The height of this form can also be adjusted for joint tension.

Figure 8:
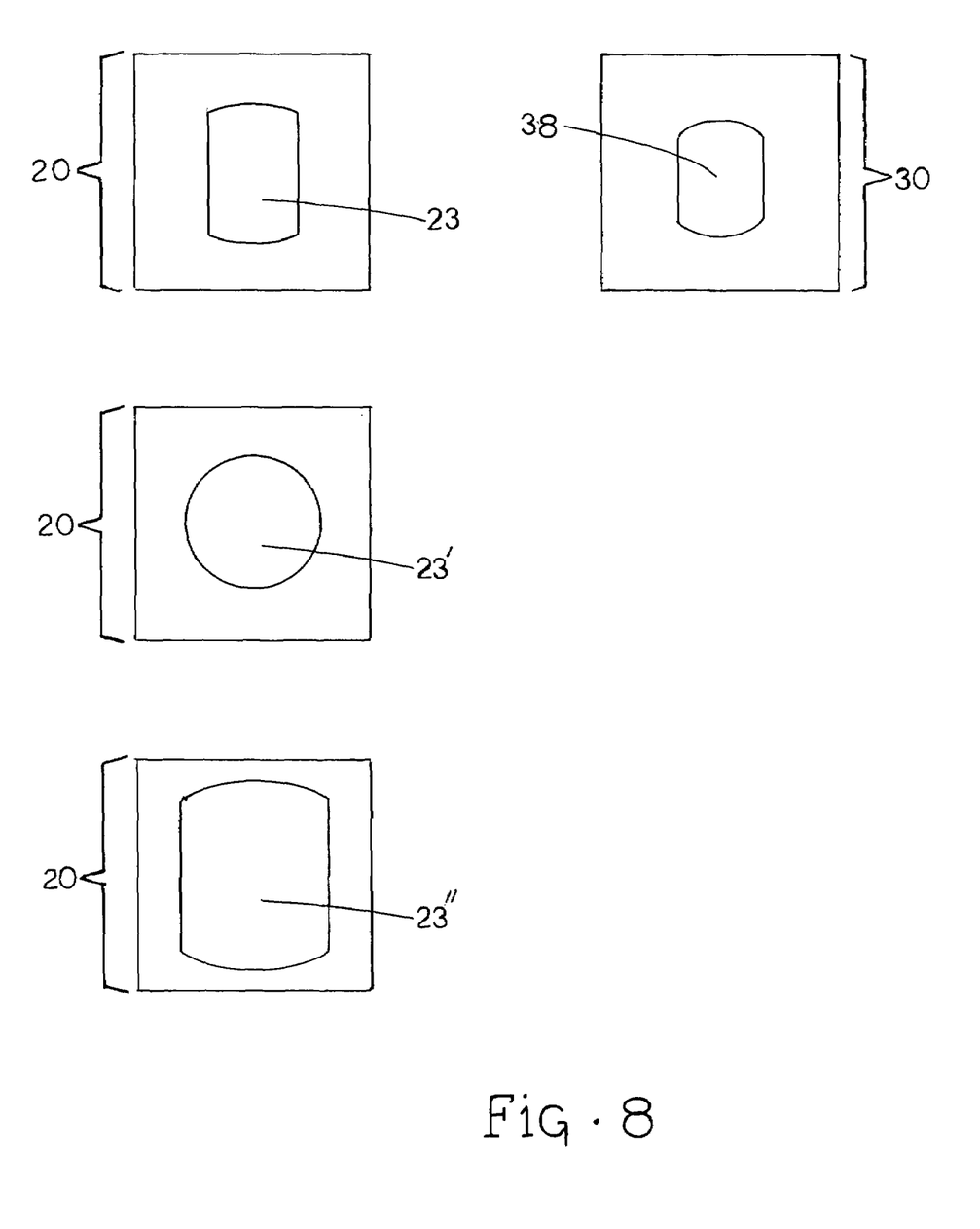
FIG. 8 of the drawings illustrates a kit having a tibial component and a plurality of bearings according to one embodiment of the present subject matter.

In yet another form, bearing component 20" as shown in FIG. 8, can have recess 23" similar to recess 23 in shape but with dimensions that can be larger to allow sliding rotational and translational movement of tibial component 30.

Figure 9:
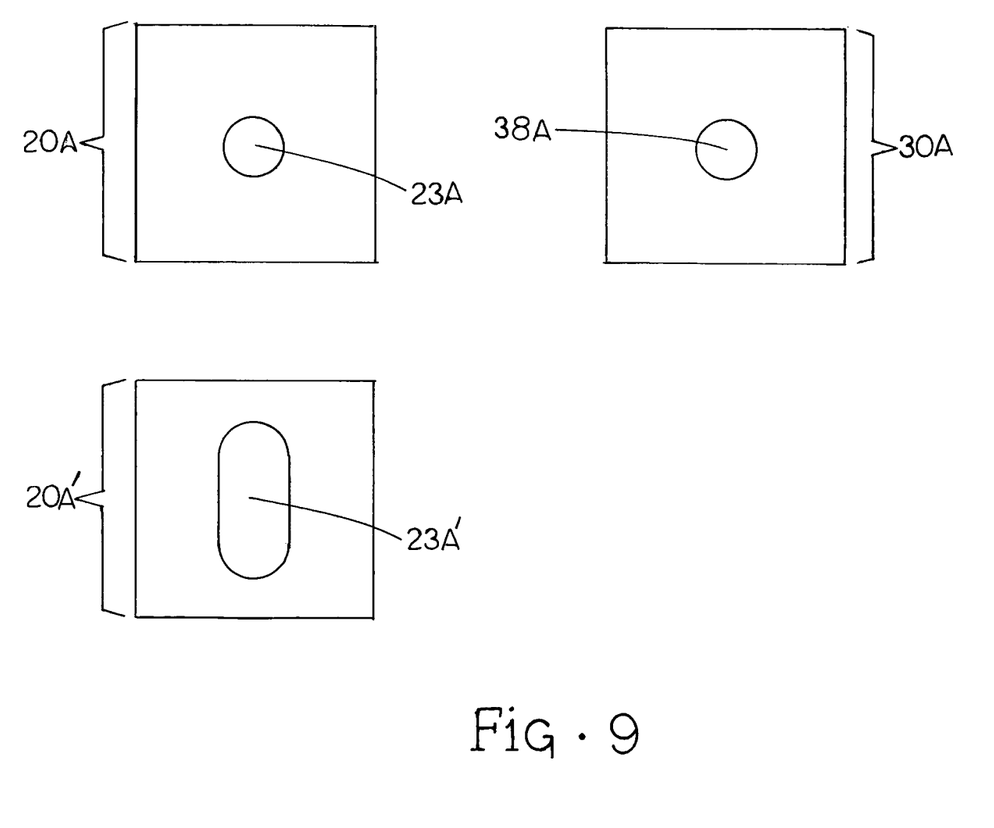
FIG. 9 of the drawings illustrates a kit having a tibial component and a plurality of bearings according to a second embodiment of the present subject matter.
Figure 10:
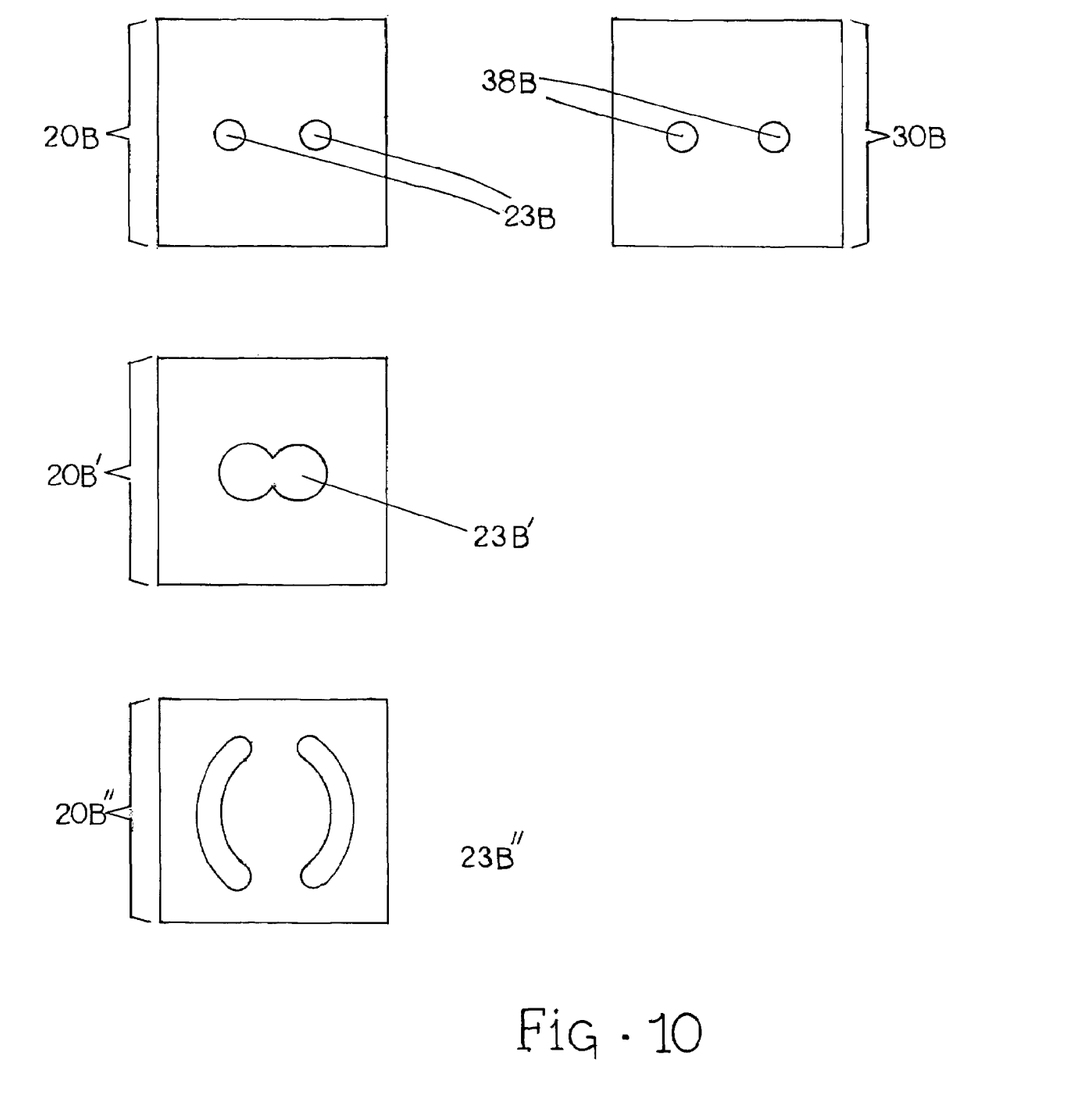
FIG. 10 of the drawings illustrates a kit having a tibial component and a plurality of bearings according to a third embodiment of the present subject matter.

FIGS. 8, 9 and 10 illustrate three examples of kits having a plurality of bearing components 20, 20', 20", 20A, 20A', 20B, 20B', 20B" that are capable of mating with their respective tibial components 30, 30A, 30B. The selection of each bearing component allows a doctor to select whether to limit rotation and translation of the joint, and to what extent, based on medical necessity and legal and regulatory limitations. These configurations as shown are provided for purposes of exemplary illustration and are not intended to be exhaustive of the types of configurations possible.

As can be appreciated by those of skill in the art, other embodiments of the present subject matter can be provided and are contemplated within the scope of the present subject matter. For example, the fixation features of the tibial and talar components could be modular. Also, the protrusion of the tibial component could be suitably rotated, such as 90 degrees, for a different set of possible ranges of motion. Similarly, the protrusion and recess features of the tibial and bearing components could be inverted so that the protrusion would extend from the bearing component with the recess defined on the tibial component instead of on the bearing component without affecting functionality. In this configuration, the protrusion could comprise one or more protrusion portions positioned on and extending from the bearing component as an integral part of the bearing component or as an attachment thereto. Such a configuration would therefore still the bearing component to be provided with a variety of suitable configurations for the protrusion portion or portions such that different bearing components could be selected for controlling or limiting range of motion as desired.

It will be understood that various details of the presently disclosed subject matter may be changed without departing from the scope of the subject matter. Furthermore, the foregoing description is for the purpose of illustration only, and not for the purpose of limitation.

What is claimed is:

1. An ankle prosthesis system comprising:
   a. a talar component having a lower surface having a bone fixation portion for fixation to a talus bone, and the talar component having an upper surface;
   b. a tibial component having an upper surface having a bone fixation portion for fixation of the tibial component to a tibia bone and/or a fibula bone, and the tibial component also having a lower surface having at least one protrusion extending from the lower surface;
   c. a plurality of bearing components for placement between the tibial and talar components, each bearing component having a lower surface for cooperative sliding engagement with the upper surface of the talar component, each bearing component also having an upper surface defining a recess, and wherein each recess is adapted for engagement with the protrusion and each recess is of a different shape to desirably and differently limit rotational and translational movement of the tibial component relative to the bearing component depending upon the bearing component utilized.

2. The ankle prosthesis apparatus according to claim 1 wherein the upper surface of the talar component is at least substantially convex.

3. The ankle prosthesis apparatus according to claim 1 wherein the lower surface of the beating component is at least substantially concave.

4. The ankle prosthesis system of claim 1 wherein the tibial component comprises a tibial attachment portion having the bone fixation portion, and a separable tibial plate portion having the protrusion.

5. The ankle prosthesis system of claim 4 further comprising a plurality of tibial plates from which a tibial plate can be selected, and wherein each tibial plate comprises a protrusion of a different shape for engagement with the recess of the bearing component.

6. A method of preparing an ankle prosthesis apparatus for installation, comprising:
   a. providing a talar component having a lower surface having a bone fixation portion for fixation to a talus bone, and the talar component having an upper surface;
   b. providing a tibial component having an upper surface having a bone fixation portion for fixation of the tibial component to a tibia bone and/or a fibula bone, and the tibial component also having a lower surface having at least one protrusion extending from the lower surface; and
   c. selecting from a plurality of bearing components, each defining a recess of a different shape, a bearing component for placement between the tibial and talar components, the bearing component having a lower surface for cooperative engagement with the upper surface of the talar component, the bearing component also having an upper surface defining a recess, wherein selection of the bearing component can provide desirable rotational and translational movement of the tibial component relative to the bearing component.

7. The method of claim 6 wherein the step of paragraph b comprises selecting the tibial component from a plurality of tibial components with each of the plurality of tibial components having a protrusion of a different shape.

8. A method of installing an ankle prosthesis apparatus comprising:
   a. installing a talar component having a lower surface having a bone fixation portion for fixation to a talus bone, and the talar component having an upper surface;
   b. installing a tibial component having an upper surface having a bone fixation portion for fixation of the tibial component to a tibia bone and/or a fibula bone, and the tibial component also having a lower surface having at least one protrusion extending from the lower surface;
   c. selecting one of a plurality of bearing components for placement between the tibial and talar components, each bearing component having a lower surface for cooperative sliding engagement with the upper surface of the talar component, each bearing component also having an upper surface defining a recess, and wherein each recess is adapted for engagement with the protrusion of the tibial component and each recess is of a different shape; and
   d. whereby rotational and translational movement of the tibial component relative to the bearing component can desirably be limited depending upon selection of the bearing component.

9. The method of claim 8 wherein the step of installing the tibial component comprises selecting the tibial component from a plurality of tibial components with each of the plurality of tibial components having a protrusion of a different shape.

* * * * *